United States Patent [19]

Liotta et al.

[11] Patent Number: 4,772,755

[45] Date of Patent: Sep. 20, 1988

[54] 1,2-1,4 ADDITION REACTION SEQUENCE LEADING TO DISUBSTITUTED ACELYLENES

[75] Inventors: Dennis C. Liotta, Stone Mountain, Ga.; Cynthia A. Maryanoff, New Hope; Vasken Paragamian, Dresher, both of Pa.

[73] Assignee: McNeilab, Inc., Springhouse, Pa.

[21] Appl. No.: 27,762

[22] Filed: Mar. 19, 1987

[51] Int. Cl.⁴ .................. C07C 43/215; C07C 43/225; C07C 39/205

[52] U.S. Cl. ................................. 568/646; 260/396 R; 564/374; 568/634; 568/744; 568/745

[58] Field of Search ............................ 260/396 R, 396; 564/374; 568/62, 780, 744, 745, 634, 646

[56] References Cited

U.S. PATENT DOCUMENTS

| | | | |
|---|---|---|---|
| 3,719,712 | 3/1973 | Remy | 564/374 |
| 4,201,638 | 5/1980 | Wan et al. | 260/396 N |
| 4,489,096 | 12/1984 | Terao et al. | 260/396 N |
| 4,661,635 | 4/1987 | Carson | 564/374 |
| 4,701,540 | 10/1987 | Lukac et al. | 547/341 |

OTHER PUBLICATIONS

Dennis Liotta, Selective Reactions of Carbonions with p-Quinones., 1981, pp. 3369, 3370.
Alfred Fischer, Reactions of Organolithium Reagents with p-Benzoquinones and Cyclohexadienones, 1979, pp. 701-704.
James A. Sinclair, Conjugate Addition of B-1-Alkynyl-9-Borabicyclo [3.3.1]-Nonanes to α, β-Unsaturated Ketones, 1976, pp. 954-956.
John Hooz, The Reaction of Diethylalkynylalane Reagents with Conjugated Enones, 1971, pp. 7320-7322.
Jerry March, Advanced Organic Chemistry (Reactions, Mechanisms, and Structure), 1977, 1968, pp. 728, 729 & 731.
Gary H. Posner, An Introduction to Synthesis Using Organcopper Reagents, 1980, pp. 1-4.
Michael Sworin, The Uncatalyzed Conjugate Addition Reaction of 2-(1,3-Dioxolan-2-Yl)-Ethylmagnesium Bromide with Cyclic α, β-Enones, 1987, pp. 3217-3220.

*Primary Examiner*—Werren B. Lone
*Attorney, Agent, or Firm*—David J. Levy

[57] ABSTRACT

A method for synthesizing a tri-substituted phenyl compound (I) by using a 1,2-addition followed by a 1,4-addition to 1,4-benzoquinone (II):

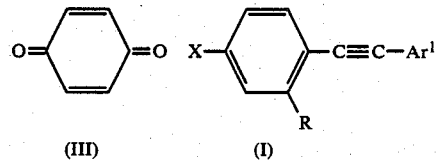

wherein X is hydroxy, alkoxy or alkanoyloxy, Ar¹ is an organic group and R is an unsubstituted or substituted alkyl group.

32 Claims, No Drawings

1,2-1,4 ADDITION REACTION SEQUENCE LEADING TO DISUBSTITUTED ACELYLENES

Various antihypertensive and antianginal acetylenes are described in European Pat. Nos. 145,361 published June 19, 1985, 146,271 published June 26, 1985 and 155,079 published Sept. 18, 1985. Anti-arrhythmic acetylenes are described in U.S. Pat. No. 3,719,712 and in the J. of Med. Chemistry, Vol. 18, No. 2, pages 142–148 (1975) and herbicidal acetylenes are described in South African Pat. No. 81/3564.

A particular synthetic problem occurs when phenyl rings have a 1,2,4-aromatic substitution pattern with an acetylenic group directly attached to the 1-position. It is an object of this invention to provide a fast, reliable synthesis of phenylacetylenes having a 1,2,4-substitution pattern on the phenyl ring, e.g. the compounds of European Pat. Nos. 145,361, 146,271 and 155,079 and precursors thereof.

SUMMARY OF THE INVENTION

A three step process is provided which comprises the reaction of a metallic acetylide (II) with 1,4-benzoquinone (III) to yield the carbinol alkoxide (IV) via a 1,2-addition:

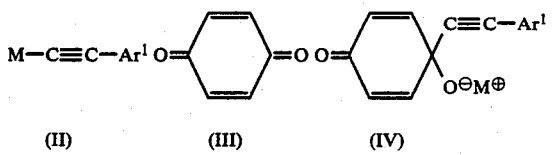

as step (a), followed by a 1,4-addition reaction of (IV) to yield enone (V) as step (b), and aromatizing the enone (V) to yield the diphenylacetylene (I) as step (c):

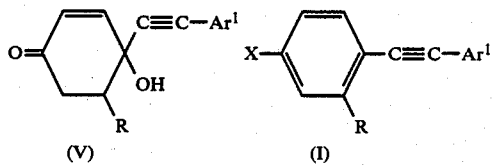

DETAILED DESCRIPTION OF THE INVENTION

The process of the present invention comprises the synthesis of a diphenylacetylene of the following Formula (I):

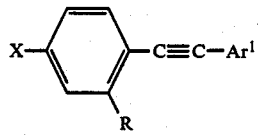

wherein
X is hydroxy, alkoxy or alkanoyloxy:
$Ar^1$ is an organic group; and
R is a substituted or unsubstituted alkyl group, which comprises the steps of:
(a) reacting an acetylide (II) with a benzoquinone (III):

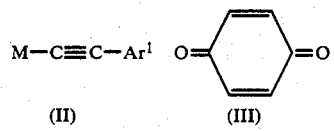

wherein M is a moiety containing a metal atom directly attached to the acetylenic carbon, by 1,2-addition to form a carbinol alkoxide (IV):

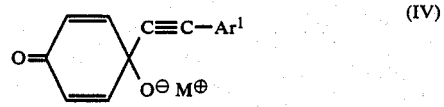

(b) reacting the alkoxide (IV) with an R-containing organomagnesium reagent to form enone (V) by 1,4-addition:

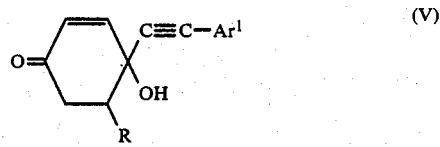

and
(c) dehydrating and aromatizing the enone (V) in the presence of a chemical means to form an X group to yield the diphenylacetylene (I).

In more detail, X is hydroxy; alkoxy of about 1 to 6 carbons such as methoxy or ethoxy; or alkanoyloxy of about 2 to 6 carbons such as acetoxy.

$Ar^1$ is phenyl which may be independently substituted by one or more of alkyl, alkoxy, alkylthio, dialkylamino, halogen or fluoroalkyl; alkyl; cycloalkyl; or alkyl substituted by dialkylamino, cycloalkyl, alkoxy, phenyl or phenyl substituted by 1 to 3 Y groups.

In particular, the optional substitution on the $Ar^1$ phenyl ring is one or more, same or different, of alkyl, alkoxy or alkylthio of about 1 to 6 carbons, such as methyl, ethyl, methoxy, iso-propoxy or methylthio; dialkylamino of about 2 to 12 carbons, e.g., of about 1 to 6 carbons in each alkyl group, such as dimethylamino or N-ethyl-N-n-propylamino; halogen such as fluoro, chloro, or bromo; or fluoroalkyl of about 1 to 6 carbons and one or more fluoro atoms with examples being 2,2,2-trifluoroethyl and trifluoromethyl. Such optional substituents may be attached at any available site on the phenyl, in particular at the meta and para positions of the phenyl ring relative to the acetylene.

In addition, $Ar^1$ can be alkyl of about 1 to 12 carbons, e.g. about 1 to 8 carbons, such as methyl, ethyl, n-butyl, iso-butyl, sec-butyl, tert-butyl, n-hexyl or n-octyl; cycloalkyl of about 5 to 7 carbons such as cyclopentyl, cyclohexyl and cycloheptyl; or an alkyl of about 1 to 6 carbons, such as methyl, ethyl, n-propyl, or iso-propyl, substituted by a dialkylamino of about 2 to 12 carbons, cycloalkyl of about 5 to 7 carbons, e.g. cyclopentyl, cyclohexyl or cycloheptyl, alkoxy of about 1 to 6 carbons such as methoxy or ethoxy, phenyl or phenyl independently substituted by 1, 2 or 3 Y groups. Y is alkyl, alkoxy, alkylthio, dialkylamino or halogen or methylenedioxy or ethylenedioxy at adjacent ring carbons. Particular Y groups are methyl, methoxy, fluoro or chloro. Alkyl groups for the dialkylamino substituents on the alkyl for $Ar^1$ include methyl, ethyl and n-propyl, particular examples being the dialkylamino groups wherein the alkyl groups are the same.

Preferably, $Ar^1$ is unsubstituted phenyl.

R may be a substituted or unsubstituted alkyl group which forms a R-containing organomagnesium compound. Examples of such compounds include Grignard reagents, e.g. as R-MgCl or R-MgBr, or di-R organomagnesium compounds, i.e., R-Mg-R. The alkyl group may be branched or straight chain from about 1 to 16 carbons and substituted with one or more of alkenyl, e.g. of about 1 to 4 carbons; a masked ketone such as a ketal (a gem-diether); a masked aldehyde such as an acetal; a dialkylamino group of about 1 to 6 carbons in each alkyl; a (phenylalkyl)alkylamino group of about 1 to 4 carbons in the alkyl groups; or such a group where the phenyl is substituted by 1, 2 or 3 alkyl or alkoxy groups of about 1 to 6 carbons. Specific examples of ketals are divalent groups attached to a non-terminal carbon of the formula —O—A—O— wherein A is an alkylene of 2 or 3 carbons which is unsubstituted or substituted by one or more alkyls of 1 to 6 carbons, e.g. —(CH$_2$)$_2$—, —(CH$_2$)$_3$— and —CH$_2$—C(CH$_3$)$_2$—CH$_2$—. Specific acetals are as described for the ketal attached to the oxo group of an aldehyde, e.g. —C(O—CH$_2$CH$_2$O)H.

R, in addition, may be of the Formula (VI) with examples of $R^1$, $R^2$, $R^3$, $R^4$, n, Alk, q and $Ar^2$ being described in European Pat. No. 146,271 and allowed U.S. Ser. No. 871,943 which is hereby incorporated by reference for said definitions as well as those of $Ar^1$:

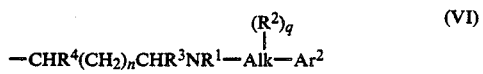
$$—CHR^4(CH_2)_nCHR^3NR^1—Alk—Ar^2 \quad (VI)$$

$R^1$ is as follows: alkyl, e.g. of about 1 to 6 carbons such as methyl, ethyl or iso-propyl; cycloalkyl, e.g. of about 3 to 6 carbons such as cyclopropyl or cyclohexyl; or cycloalkyl-alkyl, e.g. of about 4 to 7 carbons such as cyclopropylmethyl or $R^1$ is independently, i.e., independent of the value for Alk—$Ar^2$ chosen for these symbols in Formula (VI), selected from the group consisting of the defined values of —Alk—$Ar^2$, i.e., the entire list of possible —Alk— values and —$Ar^2$ values. For example, $R^1$ can be phenethyl, i.e., $R^1$ is —Alk—$Ar^2$ where Alk is ethylene and $Ar^2$ is phenyl.

$R^2$ is independently alkyl, e.g. of about 1 to 4 carbons such as methyl, ethyl or iso-propyl; or phenyl.

Alk is methylene, ethylene, trimethylene or tetramethylene, particularly ethylene.

q is 0, 1, 2 or 3, in particular 0.

n is 0, 1 or 2, in particular 1.

$Ar^2$ is phenyl; phenoxy, thiophenoxy; naphthyl, e.g. 1- or 2-naphthyl; or a 5- or 6-membered heterocyclic aromatic ring, preferably one having 1 heteroatom such as nitrogen, sulfur or oxygen, e.g. furan or thiophene attached at the 2 or 3 position, pyrrole attached at the 1 position or a 1-alkylpyrrole attached at the 2 or 3 position and pyridine attached at the 2, 3 or 4 position. The open positions of the ring, or rings in the case of naphthyl, of $Ar^2$ may be substituted by one or more, e.g. one or two, same or different, of alkyl of about 1 to 6 carbons such as methyl or ethyl; alkoxy of about 1 to 6 carbons such as methoxy and ethoxy; alkylthio of about 1 to 6 carbons such as methylthio; halogen such as fluoro, chloro and bromo; fluoroalkyl of about 1 to 6 carbons and one or more fluorine atoms with examples being 2,2,2-trifluoroethyl and trifluoromethyl; or dialkylamino of about 2 to 12 carbons such as dimethylamino; or methylenedioxy at adjacent ring carbons, particularly if $Ar^2$ is phenyl, phenoxy or thiophenoxy, e.g. 3,4-methylenedioxyphenyl.

$R^3$ is hydrogen; alkyl, e.g. of about 1 to 6 carbons such as methyl, ethyl, iso-propyl and n-pentyl; or alkoxyalkyl, e.g. of about 1 to 6 carbons in each alkyl portion such as methoxymethyl, n-butoxymethyl and ethoxyethyl.

$R^4$ is, in particular, hydrogen; or alkyl, e.g. of about 1 to 6 carbons with examples being methyl, ethyl and n-butyl.

The term "independently" is used, e.g. with respect to $Ar^1$ substitution, $R^2$ and $Ar^2$ substitution, to indicate that when more than one of such substitution is possible, such substitution may be different from each other, e.g., when q is 2, one such $R^2$ may be phenyl and the other —CH$_3$.

Compounds of Formula (I) prepared according to the process of the invention may exist in various isomeric forms, e.g., in view of the presence of an asymmetric carbon. It is understood that the invention process includes all such individual isomers and their racemates. Also within the scope of the invention are processes of the invention in which the products are in the form of hydrates and other solvate forms.

Particular compounds formed by the process of the invention may be defined as those of Formula (I) having one or more of the following definitions; X is alkoxy, particularly methoxy; R is of the Formula (VI), is —CH$_2$CH$_2$CH=CH$_2$ or is a ketal of —CH$_2$CH$_2$C(O)CH$_3$, e.g. —CH$_2$CH$_2$—C[—OCH$_2$C(CH$_3$)$_2$CH$_2$O—]CH$_3$; $Ar^1$ is phenyl or phenyl substituted with a single substituent such as chloro; $R^1$ in Formula (VI) is alkyl such as methyl; q is 0; Alk is methylene or ethylene; $Ar^2$ is phenyl or phenyl with one or two substituents such as alkoxy, e.g., methoxy, or chloro in the 3 and 4 or 3 and 5 positions; $R^3$ is hydrogen or methyl; n is 0 or 1; and $R^4$ is hydrogen.

Step (a)

By way of a 1,2-addition, acetylide (II) is reacted with 1,4-benzoquinone (III) in step (a) at a temperature of about −100° C. to +25° C. in the presence of an inert solvent. particular temperatures are about −30° C. to 0° C. and solvents are non-halogenated inert aprotic solvents such as ethers, e.g. THF, DME and Et$_2$O. Reaction times will vary depending on the temperature and nature of the $Ar^1$ moiety.

Preferably, a molar ratio for (II):(III) of 1:1 is used in step (a).

The acetylide (II) may be formed as known in the art with M moieties being alkali metals, e.g. Li, Na or K. or magnesium directly attached to the acetylenic carbon, e.g. MgBr, MgCl or MgI. The most preferred M moiety is Li. To prepare (II), the compound H—C≡C—$Ar^1$ is reacted with an M source such as an alkyl alkali metal, e.g. n-butyl lithium, an alkali amide, e.g. sodium or lithium amide, an alkyl Grignard, e.g. methyl magnesium bromide or an alkali silylamide, e.g. potassium bis(trimethylsilyl)amide. Lithium is the preferred M species and various reagents for producing LiC≡C—$Ar^1$ are found in "The Chemistry of Organolithium Compounds" ed. by B. J. Wakefield, Pergamon Press, NY (1974). The reaction conditions should be monitored to avoid the formation of diadducts to the benzoquinone, i.e., two 1,2-additions.

The carbinol alkoxide product (IV) of step (a) may be protonated to yield the dienone (VII):

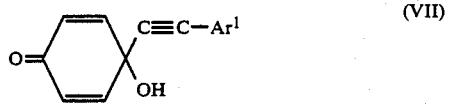

for storage or transport. The dienone may be subsequently deprotonated to reform the alkoxide (IV). The protonation can be carried out with water and the deprotonation and re-formation of the alkoxide can be accomplished with the M-containing reagent as described above.

Step (b)

In step (b), the carbinol alkoxide (IV) is reacted with an R-containing organomagnesium reagent to form the enone (V) by way of a 1,4-addition. It was surprising that the 1,4-addition took place since use of a lithium reagent for step (b), as in step (a), even in the presence of copper ion, gave a 1,2-adduct even though such would be expected to give a 1,4-adduct. With such a result for lithium in step (b), it was unexpected that an organomagnesium compound would give the 1,4-adduct. Step (b) is conducted at about $-100°$ C. to $+25°$ C., preferably about $-30°$ C. to $0°$ C., in the presence of the solvent used in step (a) and of one or more inert polar aprotic solvents such as DMF, DMSO, DMPU or HMPA. Variations of these solvents affects the ratio of 1,4:1,2 adducts in step (b). the 1,2-adduct can be separated from the reaction mixture by preparative HPLC or other chromatographic techniques.

Preferably, an equimolar ratio of (IV):R-containing organomagnesium reagent or an excess of the R-containing organomagnesium reagent is used in step (b).

The R-containing organomagnesium reagent can be a Grignard reagent, e.g. a substituted or unsubstituted alkyl magnesium halide, e.g. bromide, chloride or iodide, or can be a di(substituted or unsubstituted alkyl)-magnesium compound. Particular alkyls are unsubstituted branched or straight chain alkyls of up to 16 carbons or those substituted with an alkenyl group, a disubstituted amino group or a masked ketone as described above for R. To elaborate the R side chain to achieve the pharmacologically active compounds described in the prior art, an amine function must eventually be added.

Grignard reagents may be produced as described by E. C. Ashby in Chem Soc. Rev., Vol. 21, pages 259–285 (1967). Ketal Grignard reagents may be produced as described by J. C. Stowell in Chemical Reviews, Vol. 84, No. 5, page 409 (1984).

Step (c)

The aromatization of (V) to yield (I) can be by heating or in the presence of an acid such as HCl, a base such as $K_2CO_3$ or a salt such as pyridinium chloride in an alcohol solvent or sodium acetate in acetic anhydride. In the presence of water, the reaction product is the phenol where X is OH whereas the presence of alkanol will yield X as alkoxy and using an alkanoic acid anhydride or halide will yield X as alkanoyloxy. The heating can be at a temperature of about $25°$ to $150°$ C. depending on the particular substituents present.

As part of step (c), one may transform the R group so-produced to more fully elaborate the side chain. When one desires an ultimate product where R is of the formula (VI), an embodiment for the construction of the amine function consists of reductive alkylation of amines of the formula $R^1NH—Alk(R^2)_q—Ar^2$ by aldehydes or ketones of the formulae (I) wherein R is the ketone or aldehyde $—CHR_4(CH_2)_nCOR^3$ produced from the corresponding ketal or acetal or incipient or masked ketone or aldehyde, e.g. produced from an alkene, in the process of the invention, i.e., form steps (a), (b) and (c). The reductive alkylation may be carried out in one step from the carbonyl compound and the amine using sodium cyanoborohydride as the reducing agent in a lower alkanol or acetonitrile as the solvent at neutral to mildly acidic pH at temperatures from $0°$ to $40°$ C. Hydrogenation over a noble metal catalyst may also be used to bring about the reduction. Reductive alkylation may also be carried out in two steps. The carbonyl compound and amine are first converted to an imine or iminium salt by treatment with molecular sieves or azeotropic removal of water. Reduction is then effected by $NaBH_4$ or $NaCNBH_3$. Using the two step reductive alkylation, the alkyl groups $R^1$ and $—Alk(R^2)_q—Ar^2$ may be attached sequentially. Reductive alkylations are further described in "Advanced Organic Chemistry", 2nd Ed., by J. March, McGraw-Hill, NY (1977) at page 819.

If the initial reaction product of step (b) is an unsubstituted alkyl, the amine function may be added by two general methods after aromatization in step (c). In the first, a hydrogen on the benzylic carbon is replaced by a halogen, e.g. with $Br_2$ or $Cl_2$, as described by H. O. House in "Modern Synthetic Reactions", 2nd Edition, W. A., Benjamin Inc., Menlo Park, Ca (1972) at pages 478 to 483 and in references cited therein, particularly, 80A, 84, 85 87 and 88–91. The benzylic halogen compound is then reacted with a $\beta$-diketone of the formula alkyl—C(=O)—$CH_2$—COOALKYL as described in the "Modern Synthetic Reactions" text at pages 510–519 and references cited therein, particularly reference 12A, 13 and 15, and by W. B. Renfrow in "Journal of the American Society", Vol. 68, Sept, 1946, pages 1801–1804.

In the second method of elaborating an alkyl side chain, the benzylic compound is reacted with $[(CH_3)_2CH]_2Li$ to produce a benzylic lithium compound which may be reacted with an alkyl bromide or a bromo compound having an unprotected or protected keto function to extend the side chain as described in "Modern Synthetic Reactions" at page 514, e.g. by reaction with $BrCH_2C(=O)CH_3$ or a ketal such as $BrCH_2C(OCH_2C(CH_3)_2CH_2O)CH_3$. Such ketals may be produced as described by H. Gerlach et al. in "Helv. Chim. Acta.", Vol. 60, page 638 (1977) and by J. C. Stowell et al. in "Organic Syntheses", Vol. 62, page 140 (1984).

If the R group in (I) is a dimethylamino and if one of the alkyls is to be elaborated into an $—Alk(R^2)_qAr^2$ group as in Formula (VI), one may employ demethylation techniques as described by R. A. Olofson et al. in the J. Org. Chem, 1984, Vol. 49, pages 2081–2082, a von Braun degradation as described by T. A. Montzka et. al. in Tet. Let., 1325 (1974), in Advanced Organic Chemistry, Supra, at page 397 and in Preparative Organic Chemistry, ed. by G. Hilgetag et al., J. Wiley and Sons, NY, pages 254–255 (1972).

For transforming an R group of alkenyl-substituted alkyl to a ketone for subsequent elaboration into an amine, one may use the Wacker process as described in "Organometallics in Organic Synthesis" by J. M. Swan et al., Chapman and Hall, London (1974) at pages 130–131.

If $R^1$ is to be methyl, a methylation using formaldehyde as the carbonyl compound and sodium cyanoborohydride or sodium borohydride as the reducing agent is used.

Transformations among X groups can take place by hydrolysis of alkanoyloxy to hydroxy with mild hydroxide, by alkylation of hydroxy to yield alkoxy with an alkyl halide and by acylation of hydroxy with an acid anhydride or chloride to yield alkanoyloxy and as otherwise known in the art.

Regarding the starting materials of Formula (II), $Ar^1$-acetylenes as required may be prepared by the method of Ames et al. as described in Synthesis, 364 (1981). Treatment of $Ar^1$ iodides of the formula $Ar^1$-I with $PdCl_2[(Ph)_3P]_2$ or $Pd(OAc)_2[(Ph)_3P]_2$ and 2-methyl-3-butyn-2-ol affords acetylenic carbinols of the formula $(CH_3)_2HOC-C\equiv C-Ar^1$. Cleaveage of the carbinol with an alkali metal hydroxide gives rise to the $Ar^1$-acetylenes.

Compounds of the formula (I) wherein R is Formula (VI), including the acid-addition salts and quaternary compounds thereof, are calcium blockers, or intermediates therefor, as described in the published European patent Applications listed above and as such, are effective against angina, hypertension and cardiac arrhythmias in mammals, particularly as described by S. F. Flaim et al. in "Calcium Blockers—Mechanisms of Action and Clinical Applications", Urban and Schwarzenberg, Baltimore, MD (1982). Techniques used to determine efficacy as a calcium blocker are described by S. F. Flaim et al. in Pharmacology, Vol. 22, p. 286 to 293 (1981). The remaining compounds of Formula (I) are intermediates for those wherein R is Formula (VI) as described above.

Also part of the present invention are the enone intermediates of the Formula (V).

When used in the following Examples and throughout the specification, the following abbreviation may be used:

g (grams); mL (milliliters); mg (milligrams); M (molar); N (normal); HMPA (hexamethylphosphoramide); DMSO (dimethylsulfoxide); DMF (dimethylformamide); DMPU (1,3-dimethyl-3,4,5,6-tetrahydro-2(1H)-pyrimidinone or dimethylpropyleneurea); EtOAc (ethyl acetate); THF (tetrahydrofuran); Bu (butyl); DME (1,2-dimethoxyethane); Et$_2$O (diethyl ether); MeOH (methanol); hr (hours); min (minutes); RT (room temperature); eq (equivalents); IR (infrared); bp (boiling point); mp (melting point); HPLC (high pressure liquid chromatography); NMR (nuclear magnetic resonance); TMS (tetramethylsilane); m (multiplet); d (doublet); Hz (hertz); s (singlet); and TLC (thin layer chromatography). Unless otherwise indicated, "ether" refers to diethylether and all temperatures are in degrees centigrade.

EXAMPLE 1a

4-Hydroxy-4-(phenylethynyl)-2,5-cyclohexadiene-1-one (using n-BuLi reagent for step (a))

Phenylacetylene (5.1 mL, 0.05 mole, 1 eq) in 50 mL dry THF (distilled of Na) was introduced into a 200 mL three-necked round-bottomed flask fitted with a thermometer, condenser and argon inlet. This was cooled to −78° C., and treated with n-butyllithium (30 mL, 0.05 mole, 1 eq) in hexane. The resulting mixture was stirred for 30 min at −78° C., warmed to 0° C., stirred an additional 30 min, then added via cannula to benzoquinone (5 g, 0.05 mole, 1 eq) in 75 mL of THF at −78° C. Upon addition of the acetylide anion to the benzoquinone solution, a dark blue color appeared. The reaction was stirred for one hr at −78° C., warmed to 0° C., then poured into about 100 mL of saturated ammonium chloride solution with stirring. The resulting brown mixture was poured into a separatory funnel, about 50 mL of water and 100 mL of EtOAc added, the layers separated, and the aqueous layer extracted with three 100 mL portions of EtOAc. The organic layers were combined, washed with three 75 mL portions of brine, dried (Na$_2$SO$_4$), filtered and the EtOAc removed in vacuo to give 9.9 g of a dark brown solid. The dark brown solid was adsorbed onto silica gel and purified by flash chromatography using 4:1 hexane/EtOAc to give 8.6 g of 4-hydroxy-4-(phenylethynyl)-2,5-cyclohexadiene-1-one as a tan colored solid.

NMR(CDCl$_3$)δ(TMS): 7.4–7.2(5, m), 6.90(2, d, J=9 Hz), 6.15(2, d, J=9 Hz), 4.15(1, s).

EXAMPLE 1b 2-(2-Bromoethyl)-2,5,5-trimethyl-1,3-dioxane Grignard Reagent

Magnesium turnings (14.4 g, 0.06 mole, 3 eq) in 170 mL of dry THF were treated with dibromoethane (7.5 g). After the initial exothermic reaction had subsided, a solution of dibromoethane (30 g), 2-(2-bromoethyl)-2,5,5-trimethyl-1,3-dioxane (44.6 g) prepared by the method of J. C. Stowell et al. as described in *Organic Synthesis*, Vol. 62, p. 140 (1984), and 250 mL of THF was added dropwise over about a 7 hr period, during which time the temperature was maintained at 50° C. to 60° C. The reaction mixture was then stored in a freezer. Assay of a small portion of the Grignard solution showed that the solution was 0.28M in the title product.

EXAMPLE 1c

4-Hydroxy-4-(phenylethynyl)-5-[2-(2,5,5-trimethyl-1,3-dioxan-2-yl)ethyl]-2-cyclohexen-1-one 4-Hydroxy-4-(phenylethynyl)-2,5-cyclohexadiene-1-one (1.26 g, 0.006 mole), the compound of Example 1a and 25 mL of dry THF were placed in a dry 100 mL, three-necked round-bottomed flask under nitrogen. The reaction was cooled to −78° C. and treated dropwise with n-butyllithium (4 mL of 1.48M). The reaction was allowed to warm slowly to about 0° C. During this time, a white slurry formed. The reaction was cooled to −78° C. and treated with 4.6 mL of DMPU and one equivalent of the Grignard reagent prepared in Example 1b. The reaction was allowed to warm slowly to RT over a period of 1 hr, then quenched with ammonium chloride solution and extracted into ether. The ether extracts were washed with saturated brine and dried over anhydrous sodium sulfate. The organic phase was filtered and concentrated in vacuo. The residue was dried under vacuum overnight. The crude product was chromatographed using a flash silica gel column eluting with 1:4 EtOAc/hexane to yield a first compound-bearing fraction containing 1.5 g (68%) of the title 1,2-1,4 adduct and a third compound-bearing fraction containing 0.31 g (14%) of 1-(phenylethynyl)-4-[2-(2,5,5-trimethyl-1,3-dioxan-2-yl)ethyl]-2,5-cyclohexadiene-1,4-diol, the 1,2-1,2 adduct.

EXAMPLE 1d

4-[5-Methoxy-2-(phenylethynyl)phenyl]-2-butanone

A mixture of 4-hydroxy-4-(phenylethynyl)-5-[2-(2,5,5-trimethyl-1,3-dioxan-2-yl)ethyl]-2-cyclohexene-1-one (4 g, 0.011 mole), the title product of Example 1c, pyridinium chloride (2.5 g, 0.022 mole) and absolute methanol (30 mL) were combined and heated to reflux for 4 hr. The reaction mixture was quenched into 50 mL of water, ether was added, the resulting layers separated, the aqueous layer extracted with ether, the ether extracts combined, washed with water, brine, dried over anhydrous $Na_2SO_4$, filtered and concentrated in vacuo to give 3.0 g of the title product.

EXAMPLE 1e

N-[2-(3,4-Dimethoxyphenyl)ethyl]-5-methoxy-α-methyl-2-(phenylethynyl)benzenepropanamine 4-[5-Methoxy-2-(phenylethynyl)phenyl]-2-butanone (0.5 g, 1.8 mmole), the product of Example 1d, and homoveratryl amine (0.33 g 1.8 mmole) were combined in 10 mL of absolute methanol. With stirring, sodium cyanoborohydride (0.21 g, 3.3 mmole) was added in three portions. During this addition, the pH was adjusted to 6 with glacial acetic acid. After stirring for 5 hr, the reaction mixture was concentrated in vacuo and the resulting residue dissolved in methylene chloride. The methylene chloride solution was washed with 1N sodium hydroxide, water, brine, dried over anhydrous sodium sulfate, filtered and concentrated in vacuo to give 0.72 g of the title compound as a golden oil. The free base was dissolved in absolute methanol (5 mL) and treated with oxalic acid (0.2 g). After stirring for several hours, ether (50 mL) was added and the solution was cooled and filtered to give 1.0 g of the title compound as the oxalate salt.

EXAMPLE 1f

N-[2-(3,4-Dimethoxyphenyl)ethyl]-5-methoxy-N,α-dimethyl-2-(phenylethynyl)benzenepropanamine

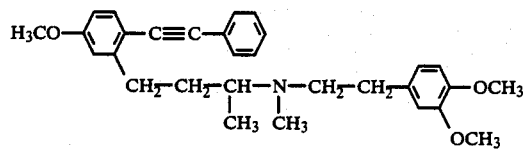

A mixture of of N-[2-(3,4-dimethoxyphenyl)ethyl]-5-methoxy-α-methyl-2-(phenylethynyl)benzenepropanamine (0.3 g, 0.68 mmole), the free base of the product of Example 1e, and 37% aqueous formaldehyde (0.5 mL) were combined in absolute methanol (5 mL). With stirring, sodium borohydride (0.05 g, 1.3 mmole) was added, and the resulting reaction mixture stirred overnight. The mixture was concentrated in vacuo, the resulting residue dissolved in 5 mL of EtOAc, 5 mL of 1N sodium hydroxide was added and the resulting layers separated. The aqueous layer was extracted with EtOAc and washed with water, brine and dried over anhydrous sodium sulfate. After filtering, the filtrate was concentrated in vacuo to give 0.3 g of the title product as a golden oil. The title product is the antihypertensive pharmaceutical prepared in Example 32 of European Pat. No. 146,271.

EXAMPLE 2

4-Hydroxy-4-(phenylethynyl)-2,5-cyclohexadiene-1-one (using LiNH₂ reagent for step (a))

A mixture of phenylacetylene (51.14 g, 0.5 mole) and dry THF (350 mL) was treated with of lithium amide (11.24 g, 0.49 mole). The mixture was heated at reflux until ammonia evolution ceased. The reaction was cooled to RT then added rapidly to a slurry of benzoquinone (47.5 g, 0.439 mole) in THF (395 mL) at −10° C. to 0° C. The reaction was stirred for about 0.5 hr then poured into an ice cold solution of ammonium chloride (68 g) in water (200 mL). The phases were separated and the aqueous phase was extracted with ether. The combined organic phases were washed with saturated sodium chloride, dried over anhydrous sodium sulfate, filtered and concentrated in vacuo. The residue was slurried with 1:1 EtOAc/petroleum ether, filtered and air dried to give 69.8 g (75.6%) of a light tan solid, the title compound.

EXAMPLE 3

4-Hydroxy-4-(phenylethynyl)-2,5-cyclohexadiene-1-one (using CH₃MgBr reagent for step (a))

Phenylacetylene (0.6 g, 0.006 mole) and 25 mL of dry THF were placed in a 50 mL, three-necked round-bottomed flask under nitrogen. Methylmagnesium bromide (2.1 mL of a 2.8 molar solution) in ether was added. The reaction was stirred for about 30 min then heated to reflux for 45 min. The reaction was allowed to cool to RT.

Benzoquinone (6.3 g, 0.006 mole) was dissolved in 25 mL of dry THF and placed under nitrogen. The reaction was cooled to −78° C. and the solution prepared above was added slowly. The reaction was stirred at −78° C. for 1.5 hr and quenched with ammonium chloride solution. The mixture was extracted with ether, the ether phase washed with saturated brine, dried over anhydrous sodium sulfate, filtered and concentrated in vacuo to give 0.91 g of a brown oil which crystallized while under vacuum. The crystals were further purified by flash column chromatography on silica using 1:4 EtOAc/hexane. The compound-bearing fractions were combined and concentrated in vacuo to yield 31% of the title 1,2-1,4 adduct.

EXAMPLE 4

4-Hydroxy-4-(phenylethynyl)-2,5-cyclohexadien-1-one (using NaNH₂ reagent for step (a))

Sodium amide (0.35 g, 0.009 mole), dry THF (25 mL), and phenylacetylene (0.92 g, 0.009 mole) were placed in a 100 mL, three-necked round-bottomed flask under nitrogen. The reaction was heated at reflux while nitrogen was blown through the flask until ammonia evolution ceased. The reaction slurry was cooled to −78° C., then added to a mixture of benzoquinone (0.97 g, 0.009 mole) in THF (50 mL) at about −108° C. The reaction mixture was allowed to warm to −30° C., then quenched into a saturated solution of ammonium chloride and extracted with ether. The ether extracts were dried over anhydrous sodium sulfate, filtered and concentrated in vacuo. The residue was chromatographed as in Example 3 to yield 0.05 g (2.6%) of the title carbinol.

EXAMPLE 5

4-Hydroxy-4-(phenylethynyl)-2,5-cyclohexadiene-1-one (using [(CH$_3$)$_3$Si]$_2$NK reagent for step (a))

A suspension of potassium bis(trimethylsilyl)amide (1.95 g, 0.0098 mole) in 20 mL of dry THF was treated with phenylacetylene (0.92 g, 0.009 mole). A flocculant white precipitate formed immediately. Benzoquinone (0.97 g, 0.009 mole) was dissolved in dry THF (10 mL) and cooled to −78° C. The potassium phenylacetylide generated above was added dropwise over a period of about 10 min. The reaction was stirred an additional 10 min, quenched by adding saturated ammonium chloride solution (20 mL) and allowed to warm to RT. The mixture was diluted with saturated ammonium chloride solution, extracted with ether and filtered to remove a flocculant dark brown precipitate. The phases were separated and the aqueous phase extracted with additional ether. The combined ether extracts were dried over anhydrous sodium sulfate, filtered and concentrated in vacuo. The residue was purified by flask chromatography on silica gel using 4:1 hexane/EtOAc as the eluent and the fractions containing the title product were combined and concentrated in vacuo to yield 0.27 g (14%).

EXAMPLE 6a

Bis(3-butenyl)magnesium

A mixture of magnesium turnings (0.5 g, 0.02 mole) and dry THF (5 mL) were placed in a dry, three-necked round-bottomed flask under argon. To this was added dropwise a solution of 2.3 g (0.7 mole) of 4-bromobutene in 5 mL of dry THF. After about ⅓ of the bromobutene was added, the reaction had not initiated. Two drops of dibromoethane was added and the reaction heated to reflux until Grignard formation was initiated. Heating was stopped and the remainder of the halide was added dropwise to maintain a gentle reflux. After all of the halide was added, the reaction was heated briefly then treated with 1.5 g (0.017 mole) of dioxane with stirring. An immediate white precipitate was formed. This suspension was used in the next step without further purification.

EXAMPLE 6b

4-Hydroxy-4-(phenylethynyl)-5-(3-butenyl)-2-cyclohexen-1-one (using (CH$_2$=CH—CH$_2$CH$_2$)$_2$Mg reagent for step (b))

Phenylacetylene (0.61 g, 0.006 mole) was added to a dry 25 mL flask containing dry THF (5 mL), n-butyllithium (4 mL of 1.48 M) and a few crystals of triphenylmethane. After stirring for several min at RT, the reaction was cooled to about 0 C., added to a flask containing benzoquinone (0.63 g, 0.006 mole) dissolved in dry THF (10 mL) and cooled to −78° C. The reaction was maintained at −35° C. to −25° during the addition. After stirring for about 15 min at −30° C., 4.6 mL of DMPU was added. The dialkylmagnesium product of Example 6a was filtered under nitrogen into the reaction mixture and the filter cake washed with ether. After stirring at −35° C. for 5 min, the reaction was allowed to warm to RT and stirred overnight. The reaction was quenched into saturated ammonium chloride solution and extracted with ether. The ether extracts were washed with saturated sodium chloride solution, dried over anhydrous sodium sulfate, filtered and concentrated in vacuo to yield 1.1 g of a mixture which was purified by flash chromatography on silica gel using 4:1 hexane/EtOAc to yield two major fractions. The first compound-bearing fraction, 0.63 g (39%) represented the desired 1,2-1,4 product. A second compound-bearing fraction, 0.51 g (32%) was the 1,2-1,2 adduct.

EXAMPLE 7a 2-(2-bromoethyl)-2-methyl-1,3-dioxolane

To a cold HBr saturated solution of ethylene glycol (210 mL) was added dropwise 118 mL of methyl vinyl ketone. The solution was allowed to warm to RT and the reaction mixture was extracted four times with pentane. The pentane layers were combined, washed with 5% sodium bicarbonate solution, dried over anhydrous magnesium sulfate and evaporated on a rotary evaporator to yield a yellow oil which was vacuum distilled to 67 g of a clear oil, bp 55°–60° C., which was the title compound.

EXAMPLE 7b

4-Hydroxy-5-[2-(2-methyl-1,3-dioxolan-2-yl)ethyl]-4-(phenylethynyl)-2-cyclohexen-1-one (Formula (V))

A solution of the product of Example 7a (9.75 g, 0.05 mole, 1.3 eq), dibromoethane (6.4 g, 0.03 mole, 0.8 eq), and 30 mL of dry THF was added over a 2.5 hr period to a slurry of 99.9% magnesium turnings (3.6 g, 0.15 mole, 3 eq) and 75 mL THF with vigorous stirring. The temperature was maintained at 24°–27° C. by external cooling. The resulting Grignard solution was then cooled to −78° C. until further use. In a separate flask, phenylacetylene (3.9 g, 0.038 mole, 1 eq) in 20 mL THF was cooled to −78° C., n-butyllithium (1.38 molar, 28 mL, 0.038 mole, 1 eq) was added via syringe, the solution stirred 30 min at −78° C., warmed to 0° C. for 30 min and cooled again to −78° C. In a separate flask, benzoquinone (4.2 g, 0.038 mole, 1 eq) in 20 mL of THF was cooled to −78° C., the phenylacetylide solution was added dropwise, resulting in a blue solution which was stirred 25 min at −78° C. DMPU (30 g, 0.23 mole, 6 eq) was added, the reaction warmed to −5° C., and the Grignard reagent solution added over about a 15 min period. The cooling bath was allowed to warm to RT and the reaction stirred overnight. The reaction mixture was quenched with 100 mL of saturated ammonium chloride solution, 100 mL of water added, the layers separated and the aqueous layer extracted with three 150 mL portions of ether. The combined organic layers were washed with water, brine and dried over anhydrous sodium sulfate. The dried solution was evaporated in vacuo to give a brown oil, 9.21 g portion of which was purified by trituration with ether followed by flash chromatography on silica gel eluting with 3:1 hexane/EtOAc to 1:1 hexane/EtOAc to yield 2.4 g of the title compound.

EXAMPLE 8

4-Hydroxy-4-(phenylethynyl)-5-[2-(2,5,5-trimethyl-1,3-dioxan-2-yl)ethyl]-2-cyclohexene-1-one Examples 8, 9 and 10 set forth experiments conducted with variations of the conditions used for the reactants of Example 1c.

Phenylacetylene (4.3 g, 0.042 mole) in dry THF (20 mL) was cooled to −78° C., treated with n-butyllithium (1.5 molar, 28.2 mL, 0.042 mole). The resulting solution was stirred at −78° C. for 30 min, warmed to 0° for 30 min and one half of the solution (about 23 mL) was removed via syringe and added to benzoquinone (2.2 g, 0.02 mole) in dry THF (20 mL) at −78° C. The resulting blue solution was stirred for 1 hr at −78° C., DMPU (15.4 g, 0.12 mole, 6 eq) was added and the mixture stirred for 5 min. The reaction mixture was warmed to about −20° C., and treated with the supernatant of the Grignard solution (71 mL, 0.02 mole) prepared in Example 1b at −78° C. The Grignard solution was added over about a 1 hr period, during which time the temperature was maintained at −5° C. to −15° C. The reaction mixture was then stirred overnight at RT. The reaction was quenched with saturated ammonium chloride solution (50 mL). Water (40 mL) was added, the resulting layers were separated, the aqueous layer extracted twice with 50 ml portions of ether. The combined ether layers were washed three times with water, once with brine, dried over anhydrous sodium sulfate, filtered and concentrated in vacuo to give 11.21 g of a dark brown oil. 10.4 g of this oil was purified by flash chromatography on silica using hexane/EtOAc (3:1 to 2:1 to 1:1) as the eluant to give 4.26 g of the 1,2 -1,4 product and 1.0 g of the 1,2-1,2 product as described in Example 1c representing corrected yields of 62% for the 1,2-1,4 product and 15% for the 1,2-1,2 product. cl

EXAMPLE 9

4-Hydroxy-4-(phenylethynyl)-5-[2-(2,5,5-trimethyl-1,3-dioxan-2-yl)ethyl]-2-cyclohexene-1-one Phenylacetylene (2.04 g, 0.02 mole) in dry THF (10 mL) was cooled to −78° C., treated with n-butyllithium (16 mL, 0.02 mole), stirred for 20 min at −78° C., warmed to 0° C. for 30 min. transferred via syringe to a separate flask containing p-benzoquinone (2.2 g, 0.02 mole) in THF (10 mL) and cooled to −78° C. The resulting blue solution was then stirred 1 hr at −78° C., DMPU (15.4 g, 0.12 mole, 6 eq) was added, stirred for 5 min and warmed to −20° C. The Grignard solution from Example 1b was warmed to RT, stirred and allowed to settle. The supernatant from the Grignard solution (83 mL, 0.02 mole) was removed via syringe, introduced into a constant addition funnel and added to the alkoxide over a 1 hr period. After 30 mL were added, the mixture had warmed to 5° C. The mixture was then cooled down to −10° C. and maintained at −10° C. for the rest of the addition taking 1 hr. The reaction was stirred at RT overnight, quenched with 50 mL of saturated ammonium chloride solution and 40 mL of water were added. After the layers separated, the aqueous layer was extracted twice with 50 mL portions of ether. The organic layers were combined, washed with three portions of water and one portion of brine, dried over anhydrous sodium sulfate, filtered and concentrated in vacuo to give 10.55 g of a dark brown oil of which 9.91 g was purified by flash chromatography on silica using hexane/EtOAc (3:1 to 2:1 to 1:1) to give five major fractions. The product-bearing fractions contained 3.1 g (45%) of the 1,2-1,4 product and 1.7 g (25%) of the 1,2-1,2 product both as named in Example 1c.

EXAMPLE 10

4-Hydroxy-4-(phenylethynyl)-5-[2-(2,5,5-trimethyl-1,3-dioxan-2-yl)ethyl]-2-cyclohexene-1-one Into a dry, 25 mL three-necked round-bottomed flask fitted with a mechanical stirrer, thermometer and argon inlet were introduced several crystal of triphenylmethane, about 3 mL of 1.5M n-butyllithium and dry THF (3 mL) (distilled over sodium). The resulting red solution was treated with phenylacetylene (0.53 g, 0.005 mole) until the red color was quenched. Into a separate dry 100 mL, three-necked round-bottomed flask similarly outfitted was introduced of p-benzoquinone (0.56 g, 0.005 mole) and dry THF (3 mL). This was cooled to −4° C. and then treated with the phenylacetylide solution added via syringe. The conversion to alkoxide was complete in about 20 min. After stirring for 30 min at −4° C., the alkoxide was treated with 4 g of DMPU (dried over sieves). The alkoxide solution was allowed to warm briefly to 15° C., then cooled to 10° C. with a color change from blue to brown. A portion (21 mL, 0.05 mole, 1 eq) of the Grignard reagent prepared as in Example 1b was added. The reaction was allowed to warm to RT and stirring continued overnight. The reaction mixture was quenched with 30 mL of saturated ammonium chloride, 30 mL of water were added, and the layers separated. The aqueous layer was extracted twice with 30 mL portions of ether. The organic layers were combined, washed with three 30 mL portions of water, one 30 mL portion of brine, and dried over anhydrous sodium sulfate. After filtering, the filtrate was concentrated in vacuo to yield 2.29 g of an oil. HPLC of the product showed the mixture to contain 13.1% of the 1,2-1,2 product and 37.2% of the 1,2-1,4 product both as named in Example 1c.

EXAMPLE 11a 2-(2-Chloroethyl)-2,5,5-trimethyl-1,3-dioxane

A 1-liter, three-necked round-bottomed flask was fitted with a mechanical stirrer, gas inlet tube and oil bubbler. In the flask were placed 350 mL of methylene chloride, distilled methyl vinyl ketone (70 g, 1 mole), and dicinnamalacetone indicator (about 0.01 g). The solution was cooled to 0° C. and hydrogen chloride gas bubbled through until a deep red color persisted. The cooling bath was removed and 2,2-dimethyl-1,3-propanediol (104 g, 1 mole) triethylorthoformate (148 g, 1 mole) and p-toluenesulfonic acid (0.67 g) were added. The reaction mixture was capped with argon and stirred at RT for 2½ hr. The mixture was then concentrated in vacuo, about 100 mL of saturated sodium bicarbonate solution added and the layers separated. The organic phase was washed again with saturated sodium bicarbonate solution and the aqueous layers combined, extracted twice with methylene chloride and the organic layers combined, washed with brine and dried over anhydrous sodium sulfate. After filtering, the methylene chloride solution was evaporated in vacuo to give 190.5 g of a golden oil. The oil was distilled under reduced pressure at 0.3 mm Hg, at 60° C. to 64° C. to give 146.3 g of a mixture which was purified by preparative HPLC using 2% EtOAc/hexane to give 133.5 g of a clear oil which was used in the next step without further purification.

EXAMPLE 11b

4-Hydroxy-4-(phenylethyl)-5-[2-(2,5,5-trimethyl-1,3-dioxan-2-yl)ethyl]-2-cyclohexen-1-one (using a Grignard prepared from a chloro compound)

Magnesium turnings (2.2 g, 0.09 mole) and THF (50 mL) (dried over sodium) were introduced into a 300 mL, three-necked round-bottomed flask fitted with a condenser, thermometer, magnetic stirring bar and an argon inlet. Dibromoethane (1.12 g, 0.006 mole, 0.2 eq)

was added. After the initial exothermic reaction had subsided, a solution of the chloroketal (5.8 g, 0.03 mole) from Example 11a, dibromethane (4.5 g, 0.024 mole, 0.8 eq) and THF (25 mL) were added over a 2 hr period via syringe while the temperature was maintained about 55° C. The Grignard reaction was then heated an additional 2 hr.

Phenylacetylene (1.47 g, 0.014 mole) in THF (10 mL) was cooled to −78° C., 1.4M n-butyllithium (10.5 mL, 0.014 mole) was added dropwise and the reaction was stirred 20 min at −78° C., warmed to 0° C. for 20 min, recooled to about −30° C. and then added via syringe to benzoquinone (1.56 g, 0.014 mole) in 10 mL THF at −78° C. The resulting blue solution was stirred at −78° C. for 20 min, warmed to −10° C., DMPU (11.1 g, 0.09 mole, 6 eq) was added, stirred for 5 min. The above Grignard solution was added via constant addition funnel over a 1 hr period, during which time the temperature was maintained at −5° C. to −10° C. The reaction was then allowed to stir overnight at RT. The reaction was quenched with 100 mL of saturated ammonium chloride solution: 100 mL of water and 50 mL of ether were added and the layers were separated. The aqueous layer extracted with three 75 mL portions of ether, the organic layers combined and washed with two 75 mL portions of water, one 75 mL portion of brine and dried over anhydrous sodium sulfate. After filtering, the filtrate was concentrated in vacuo to give 7.28 g of a tan oil. The oil was purified by flash chromatography on silica gel using hexane/EtOAc (3:1 to 1:1) as the eluant to give two major products which consisted of 1.7 g (35%) of the 1,2-1,4 product and 0.7 g (15%) of the 1,2-1,2 product, both as named in Example 1c.

EXAMPLE 12

4-Hydroxy-4-(phenylethynyl)-5-[2-(2,5,5,-trimethyl-1,3-dioxan-2-yl)ethyl]-2-cyclohexen-1-one (using DMF as a solvent)

Several crystals of triphenylmethane and 1.5M n-butyllithium (3 mL) and 3 mL of dry THF (distilled over sodium) were introduced into a dry 25 mL three-necked round-bottomed flask, fitted with a mechanical stirrer, thermometer and argon inlet. The resulting red solution was treated with phenylacetylene added dropwise until the red color was quenched (0.54 g, 5.3 mmole). The reaction exothermed to 33° C. during the phenylacetylene addition. Into a separate 100 mL, dry, three-necked round-bottomed flask was introduced benzoquinone (0.57 g, 5.3 mmole) and of dry THF 3 mL. The solution was cooled to −78° C., treated with the phenylacetylide solution. The resulting blue mixture was stirred 50 min at −78° C. DMF (2.3 g, 32 mmole, 6 eq, dried over sieves) was added and the mixture was stirred for 2 hr. The Grignard reagent (26 mL of 0.21M, 5.3 mmole, 1 eq) prepared as in Example 1b was cooled to 31 78° C. then the supernatent was added dropwise over a 15 min period. The reaction was stirred at −78° C. for 15 min, allowed to warm to RT, and stirred overnight. The reaction was quenched with 30 mL of saturated ammonium chloride solution, 30 mL of water added, the layers separated, the aqueous layer extracted twice with 30 mL portions of ether, the combined ether layers washed with three 30 mL portions of water, one 30 mL portion of brine, dried over anhydrous sodium sulfate, filtered and concentrated in vacuo to give 3.04 g of product which consisted of 31.0% 1,2-1,2 isomer and 23.1% of the 1,2-1,4 isomer.

EXAMPLE 13

4-Hydroxy-4-(phenylethynyl)-5-[2-(2,5,5-trimethyl-1,3-dioxan-2-yl)ethyl]-2-cyclohexene-1-one (using DMSO as a solvent)

n-Butyllithium (3.2 mL 1.5M) was introduced into a dry, 25 mL, three-necked round-bottomed flask fitted with a mechanical stirrer, thermometer and argon inlet. Several crystals of triphenylmethane and dry THF (3 mL) was added producing an orange-red color. Phenylacetylene (0.58 g, 0.0057 mole) was added until the red color was quenched to yellow. In a separate flask, benzoquinone (0.61 g, 0.0057 mole) and dry THF (3 mL) were introduced, cooled to −78° C. and were treated with the phenylacetylide solution via syringe. The resulting blue solution was stirred 30 min at −78° C. and DMSO (2.7 g, 0.034 mole, 6 eq) was added via syringe. The mixture was stirred 1 hr at −78° C. and warmed to −20° C. at which point the mixture became homogeneous. The supernatent from a Grignard solution (23 mL of 0.245M, 0.0057 mole, 1 eq) prepared by the method in Example 1b was added dropwise over a 30 min period during which time the reaction temperature was maintained at −10° C. to −15° C. The reaction was then allowed to warm to RT, stirred overnight and quenched with 30 mL of saturated ammonium chloride solution. Water (30 mL) was added and the layers were separated; the aqueous layer was extracted twice with 30 mL portions of ether, the ether layers combined, washed three times with 30 mL portions of water, once with brine, dried over anhydrous sodium sulfate, filtered and concentrated in vacuo to yield 2.73 g of a mixture which consisted of 26% of the 1,2-1,2 product and 49% of the 1,2-1,4 product as named in Example 1c.

EXAMPLE 14

4-Hydroxy-4-(phenylethynyl)-5-[2,5,5-trimethyl-1,3-dioxan-2-yl)ethyl]-2-cyclohexene-1-one (using HMPA as a solvent)

n-Butyllithium (3 mL of 1.5M) was introduced into a dry, 25 mL, three-necked round-bottomed flask. Dry THF (3 mL) and several crystals of triphenylmethane were added. Phenylacetylene (0.5 g, 4.9 mmole) was added dropwise until the red solution was quenched to a gold-yellow color. In a separate flask, benzoquinone (0.53 g, 4.9 mmole) in 3 mL of dry THF was cooled to −78° C. and treated with the phenylacetylide solution. The resulting blue solution was stirred 1 hr at −78° C., HMPA (5.3 g, 29 mmole, 6 eq, dried over sieves) was added, the reaction mixture stirred for 2 hr at −78° C. and the supernatent from a Grignard solution (25 mL of 0.2M, 4.9 mmole, 1 eq) prepared as in Example 1b was added over a 15 min period. The reaction was then stirred at −78° C. for an additional 15 min, allowed to warm to RT, stirred overnight and quenched with 30 mL of saturated ammonium chloride solution. Water (30 mL) was added, the layers separated, the aqueous layer extracted twice with 30 mL portions of ether, the ether layers combined, washed four times with 30 mL portions of water and one 30 mL portion of brine, dried over anhydrous sodium sulfate, filtered and concentrated in vacuo to give 2.49 g of a brown oil which consisted of 15.8% of the 1,2-1,2 product and 61% of the 1,2-1,4 product both as named in Example 1c.

EXAMPLE 15

3-[2-(2-Methyl-1,3-dioxolan-2-yl)ethyl]-4-(phenylethynyl)phenyl acetate (Formula (I), X=CH$_3$CO—)

4-Hydroxy-5-[2-(2-methyl-1,3-dioxolan-2-yl)ethyl]-4-(phenylethynyl)-2-cyclohexen-1-one (3.0 g, 9.2 mmole, prepared in a manner similar to that in Example 7b) was dissolved in acetic anhydride (25 mL) and stirred at RT under argon. After stirring 5 hr at RT, the reaction mixture was heated to reflux overnight. The reaction mixture was cooled to RT, poured into about 100 mL of ether, about 200 mL of saturated sodium bicarbonate added and the solution stirred. After evolution of CO$_2$ was complete, solid sodium bicarbonate was added cautiously until foaming ceased. The layers were separated, the aqueous layer extracted twice with 100 mL portions of ether, the ether layers combined, washed with two 100 mL portions of sodium bicarbonate solution, two 100 mL portions of ether, the ether layers combined, washed with two 100 mL portions of saturated sodium bicarbonate solution, two 100 mL portions of water and 75 mL of saturated brine. After drying over anhydrous sodium sulfate, the organic layer was filtered and concentrated in vacuo to give 3.2 g of the title compound, a dark orange oil.

EXAMPLE 16a

4-Chloro-1-butene Grignard Reagent

Magnesium turnings (7.2 g, 0.03 mole) were placed in 15 mL of dry DME. Several drops of dibromoethane were added to initiate the reaction and 4-chloro-1-butene (9.0 g, 0.1 mole) in 35 mL of DME was added dropwise while the reaction was stirred and heated at reflux. After 3 hr, the heating was stopped and the reaction was allowed to stand at RT overnight.

1 mL of the solution prepared above was placed in a 100 mL three-necked round-bottomed flask, diluted with dry DME (20 mL) and treated with 2,2'-dipyridyl. A reddish-brown solution resulted. A solution of menthol (1 g) in 10 mL of dry DME was added slowly until the red color was discharged. The calculated molarity of the Grignard solution was 0.64M. This solution was used in the next step without further purification.

EXAMPLE 16b 5-(3-Butenyl)-4-hydroxy-4-(phenylethynyl)-2-cyclohexene-1-one and 1-(3-butenyl)-4-(phenylethynyl)-2,5-cyclohexadiene-1,4-diol (using DME as a solvent)

Phenylacetylene (0.6 g, 0.006 mole) and lithium amide (0.14 g, 0.006 mole) were taken up in 30 mL of DME, heated at 50° C. to 55° C. until ammonia evolution ceased, cooled and added to benzoquinone (0.63 g, 0.006 mole) in dry DME (15 mL) at −78° C. The reaction was stirred at −78° C. for several minutes, warmed to 0° C., cooled to −78° C. and DMPU (4.6 mL) was added, followed by 10 mL of the Grignard solution prepared in Example 16a. The reaction was maintained at −78° C. for about 3 hr, allowed to warm slowly to RT, stirred overnight and quenched with 30 mL of saturated ammonium chloride solution, diluted with water and extracted with ether. The organic phase was washed with three 50 mL portions of water, brine and dried over anhydrous sodium sulfate. The drying agent was removed by filtration and the organic extracts were concentrated under reduced pressure to yield 1.32 g of the crude title compound. The residue was chromatographed using a flash silica gel column and 50% EtOAc/hexane. The product-bearing fractions were combined and concentrated in vacuo to yield 0.92 g of the 1,2-1,4 title compound and 0.17 g of the 1,2-1,2 title compound, respectively.

EXAMPLE 17

5-(3-Butenyl)-4-hydroxy-4-(phenylethynyl)-2-cyclohexen-1-one and 1-(3-butenyl)-4-(phenylethynyl)-2,5-cyclohexadiene-1,4-diol (using THF as a solvent)

A 100 mL, three-necked round-bottomed flask was dried using a heat gun while a stream of argon was blown through the flask. Magnesium turnings (0.5 g, 0.02 mole) and THF (5 mL) were placed in the flask. 4-Chlorobutene (1.5 g, 0.017 mole) was diluted with dry THF (5 mL) and about ⅓ of the solution was added. A small crystal or iodine was added and the reaction was heated at reflux while the halide solution was added dropwise over a period of 1 hr. After the addition, the reaction was refluxed an additional 3 hr, allowed to cool to RT and titrated for Grignard content which was found to be 0.00136 mole/mL.

Phenylacetylene (0.6 g, 0.006 mole) was added slowly to a dry, 50 mL, pear-shaped flask containing dry THF (5 mL) and n-butyllithium (4 mL of 1.48M) and a crystal of triphenylmethane. The color was discharged upon addition of the last drop of phenylacetylene. This solution was added slowly to benzoquinone (0.63 g, 0.006 mole) in dry THF (10 mL) at −78° C. The reaction was allowed to warm slowly to 0° C., cooled to −78° C. and DMPU (4.6 mL) was added rapidly. A portion (4.4 mL) of the Grignard solution prepared above was added over a period of about 5 min. The reaction was stirred at −78° C. for 1 hr, allowed to warm slowly to RT and stirred overnight. The reaction was quenched using 40 mL of saturated ammonium chloride solution, extracted with ether and the combined ether extracts were washed with three 50 mL portions of water and brine and dried over anhydrous sodium sulfate. After filtering, the filtrate was concentrated in vacuo to yield 1.7 g of an oil. This oil was chromatographed through a flash silica gel column using 1:1 EtOAc/hexane. The first compound-bearing fraction contained 1.1 g (69%) of the 1,2-1,4 title product and the second compound-bearing fraction contained 0.14 g (8.8%) of the 1,2-1,2 title product, respectively.

EXAMPLE 18

5-(3-Butenyl)-4-Hydroxy-4-(phenylethynyl)-2-cyclohexene-1-one and 1-(3-butenyl)-4-(phenylethynyl)-2,5-cyclohexadiene-1,4-diol (using DME and Et$_2$O as solvents)

Phenylacetylene (0.6 g, 0.006 mole) was placed in a dry, 50 mL, three-necked round-bottomed flask and diluted with dry DME (5 mL). n-Butyllithium (4 mL of 1.48M solution) was added dropwise over a 5 min period. The reaction was allowed to stand at RT while a solution of benzoquinone (0.63 g, 0.006 mole) in dry DME (10 mL) was prepared at −78° C. The lithium phenylacetylide solution prepared above was added over a period of about 5 min followed by DMPU (4.6 mL). A Grignard reagent was prepared from magnesium turnings 1.6 g and 4-chlorobutene (14.9 g) in 50 mL of ether. This reagent was assayed for Grignard content. One molar equivalent of the Grignard reagent was added to the original reaction flask and the mixture allowed to warm slowly to RT and stirred overnight. The reaction was quenched with 35 mL of saturated ammonium chloride solution and extracted with ether. The combined ether extracts were washed with water and brine and dried over anhydrous sodium sulfate. After filtering, the filtrate was concentrated in vacuo to yield an oil which was purified by flash column chromatography using 1:1 EtOAc/hexane as the eluant. The product-bearing fractions yielded 0.9 g (56%) of the 1,2-1,4 adduct title product and 0.06 g (3.8%) of the 1,2-1,2 adduct title product, respectively.

EXAMPLE 19

4-Hydroxy-5-[2-(2-methyl-1,3-dioxolan-2-yl)-ethyl]-4-(phenylethynyl)-2-cyclohexen-1-one This Example was conducted in a manner similar to Example 7b except that the alkoxide was maintained at $-78°$ C. as opposed to $-5°$ C.

Magnesium turnings (2.7 g, 0.011 mole, 6 eq) and 5 mL of dry THF were introduced into a 50 mL, three-necked round-bottomed flask fitted with a thermometer, liquid addition funnel and argon inlet. A solution of 2-(2-bromoethyl)-2-methyl-1,3-dioxolane (7.2 g (0.037 mole, 2 eq, the compound of Example 7a) prepared by the method of H. Gerlach, et al., *Helv. Chem.*, Vol. 60, p. 638 (1977) in THF (5 mL) was added dropwise, during which time the temperature was maintained at 27° C. to 29° C. Grignard formation was initiated with several drops of 1,2-dibromoethane. In a separate 50 mL, round bottomed flask outfitted in a similar manner was introduced phenylacetylene (2.0 mL, 0.019 mole, 1 eq) in THF (5 mL) which was cooled to $-78°$ C. and n-butyllithium (11.6 mL, 0.019 mole, 1 eq of 1.6M) was added. The resulting solution was stirred for 1 hr, warmed to 0° C., for 30 min, cooled again to $-78°$ C. In a separate 100 mL, round bottomed flask fitted with a mechanical stirrer, thermometer and argon inlet, p-benzoquinone (2 g, 0.019 mole, 1 eq) in THF (5 mL) was introduced and cooled to $-78°$ C. The phenylacetylide solution was warmed to $-30°$ C. to maintain homogeneity, added via cannula to the benzoquinone solution above, the resulting blue-green solution was stirred for 5 min and DMPU (13.4 mL, 0.11 mole, 6 eq) was added. The reaction became dark blue was stirred for 20 min and the ketal Grignard was added dropwise via syringe. After addition was complete, the cooling bath was removed. An exotherm was noted at this point. After stirring about 1 hr at RT, the reaction mixture became fluid and two layers were observed. The reactions was then stitted at RT for two days, quenched with 50 mL of saturated ammonium chloride solution, 50 mL of water and the mixture extracted with ether. The ether layers were washed with water and brine, dried over anhydrous sodium sulfate, filtered and the ether removed in vacuo to give 6.85 g of a tan oil. The oil was purified by flash chromatography on a silica column using hexane/EtOAc (3:1 to 1:1) as the eluant to yield two major products. The first compound-bearing fraction, 2.9 g (48), contained the 1,2-1,4 title product adduct and the second compound-bearing fraction, 0.92 g (15%), contained the 1,2-1,2 adduct.

EXAMPLE 20

4-Hydroxy-4-(phenylethynyl)-5-[2-(2,5,5-trimethyl-1,3-dioxan-2-yl)ethyl]-2-cyclohexene-1-one ($-24°$ C. for step (a) and $-20°$ C. for step (b))

Into a dry, 25 mL, three-necked round-bottomed flask fitted with a thermometer, magnetic stirring bar and argon inlet was n-butyllithium (3 mL of 1.5M) and several crystals of triphenylmethane were introduced. Dry THF (3 mL) (distilled over sodium) was added, resulting in a red solution to which was added phenylacetylene (0.52 g, 0.0051 mole). In a separate, 100 mL dry, three-necked around-bottomed flask fitted with a mechanical stirrer, thermometer and nitrogen inlet was introduced p-benzoquinone (0.55 g, 0.0051 mole, 1 eq) in dry THF (3 mL). The flask was then suspended in a 50% water-ethylene glycol solution, cooled to $-24°$ C. in a constant temperature bath. The lithium phenylacetylide solution from above was added via syringe. The solution was stirred for 30 min, DMPU (3.9 g, 0.03 mole, 6 eq, dried over sieves) was added and the solution stirred 1.5 hr at $-20°$ C. A Grignard solution (22 mL, 0.0051 mole, 1 eq of 0.232M) prepared as in Example 1b was added via syringe, the mixture stirred 3 hr at $-20°$ C., the cooling bath and mechanical stirring removed and the reaction kept under nitrogen overnight. The reaction was quenched with 30 mL of saturated ammonium chloride solution, 20 mL of water were added, the layers separated, the aqueous layer extracted twice with ether, the organic layers combined, washed twice with water, once with brine, dried over anhydrous sodium sulfate, filtered and concentrated in vacuo to give 2.62 g of a dark brown oil. Assay by HPLC indicated that 42% of the dark brown oil was the 1,2-1,4 title adduct and 14% was the corresponding 1,2-1,2 adduct.

EXAMPLE 21

4-Hydroxy-4-(phenyethynyl)-5-[2-(2,5,5-trimethyl-1,3-dioxan-2-yl)ethyl]-2-cyclohexene-1-one ($-24°$ C. for step (a) and 0° C. for step (b))

Following the procedure of Example 20, with the exception that the reaction was run at 0° C. instead of $-20°$ C., there was obtained 2.59 g of a dark brown oil which contained by HPLC assay 36% of the 1,2-1,4 title adduct and 15% of the corresponding 1,2-1,2 adduct-both as named in Example 1c.

EXAMPLE 22

4-Hydroxy-4-(phenylethynyl)-5-[2-(2,5,5-trimethyl-1,3-dioxan-2-yl)ethyl]-2-cyclohexene-1-one ($-78°$ C. for step (a) and $-20°$ C. for step (b))

Magnesium turnings (0.8 g) were introduced into a 100 mL three-necked round-bottomed flask fitted with a condenser, magnetic stirring bar, thermometer and argon inlet. The flask and magnesium were then dried with a heat gun, dry THF (60 mL, distilled over sodium) was introduced, followed by the ketal (6 g 0.025 mole) of Example 1b. The mixture was then heated to reflux for 30 min and assayed for Grignard reagent. The assay showed the molarity of the reagent to be 0.226M.

In a separate, dry, 50 mL, three-necked round-bottomed flask was introduced several crystals of triphenylmethane, n-butyllithium (7.9 mL of 1.5M) and dry THF (8 mL). To the resulting red solution was added dropwise Phenylacetylene (1.4 g, 0.013 mole) until the red color was quenched.

In a separate, dry, 300 mL, round bottomed flask was introduced p-benzoquinone (1.4 g, 0.013 mole, 1 eq) and dry THF 10 mL, cooled to −78° C., and treated with the above lithium phenylacetylide solution. The resulting blue solution was stirred at −78° C. for 45 min, DMPU (10.2 g, 0.08 mole, 6 eq) (dried over sieves) was added, stirred 15 min, the solution warmed to −20° C. and the Grignard solution prepared above was added dropwise over a 20 min period while maintaining the temperature at −20° C. to −25° C. The solution was then stirred 15 min at −20° C. and the cooling bath removed. The reaction was allowed to warm to RT and stir for two days. The reaction was quenched with 50 mL of saturated ammonium chloride solution, 50 mL of water added, the layers separated, the aqueous layer extracted twice with ether and the organic layers combined, washed with water, brine, dried over anhydrous sodium sulfate, filtered and concentrated in vacuo to yield 6.36 g of an oil. Assay by HPLC indicated that the oil contained 59% of 1,2-1,4 adduct and 15% of 1,2-1,2 adduct.

EXAMPLE 23a

5-[2-(N,N-Dimethylamino)propyl]-4-hydroxy-4-(phenylethynyl)-2-cyclohexen-1-one (steps (a) and (b) at −78° C.)

To a −78° C. solution of phenylacetylene (1.00 g, 9.79 mmole) in THF (25 mL) was added by syringe n-BuLi (10.8 mL, 0.91M in hexane, 9.79 mmol). After stirring for 0.5 hr at −78° C., the reaction was allowed to warm to 0° C. and stir for 30 min. At this time, the solution of lithium phenylacetylide was added dropwise by cannula to a −78° C. solution by p-benzoquinone (1.01 g, 9.32 mmol) in THF (50 mL). After stirring for 5 min at −78° C., a solution of the Grignard BrMg(CH$_2$)$_3$N(CH$_3$)$_2$ (12.3 mL, 1.6M in THF) and 1,3-dimethyl-3,4,5,6-tetrahydro-2(1H)-pyrimidinone (13.5 mL, 112 mmol) was added by cannula. The cold bath was then removed and the reaction was allowed to warm to 23° C. At RT, the reaction was quenched by addition to H$_2$O and Et$_2$O. After separating the organic phase, the aqueous phase was saturated with NaCl and extracted with Et$_2$O (3 times). The combined organic phases were then dried (MgSO$_4$) and evaporated leaving a brown oil. Crystallization from Et$_2$O gave 1.50 g of the desired title enone product as light brown prisms. The mother liquor was then subjected to column chromatography (flash SiO$_2$; 20% MeOH/CHCl$_3$ and 0.1% NH$_4$OH) to give an additional 200 mg (total yield=61%). Recrystallization from EtOAc/hexane gave yellow prisms mp 131° C.-133° C.

EXAMPLE 23b

3-[5-Mesyl-2-(phenylethynyl)phenyl]-N,N-dimethylpropanamine

To a 23° C. solution of the enone product of Example 23a (558 mg, 1.88 mmol), was added methanesulfonyl chloride (0.32 mL, 4.12 mmol) followed by triethylamine (0.78 mL, 5.64 mmol). After stirring for 1 hr at 23° C., the reaction was partitioned between saturated aqueous NaHCO$_3$ and EtOAc. The organic phase was then separated, dried (MgSO$_4$) and evaporated to give 600 mg of a brown oil. This oil was subjected to column chromatography (7% MeOH/CHCl$_3$ and 0.1% NH$_4$OH) to give 564 mg of the mesylate title product as a pale yellow oil (84% yield); IR (neat. cm$^{-1}$): 1372, 1182.

EXAMPLE 23c

3-[5-Hydroxy-2-(phenylethynyl)phenyl]-N,N-dimethylpropanamine

A solution of the mesylate product of Example 23b (564 mg, 1.58 mmol) in 1N KOH/MeOH was stirred for 3 hr at 23° C. At this time, a thick precipitate was present. After partitioning between EtOAc and pH 7 phosphate buffer (acidified to pH 7 with several drops of concentrated HCl), the aqueous phase was extracted with EtOAc (3 times) and CHCl$_3$ (3 times). Since TLC (20% MeOH in CH$_2$Cl$_2$ and NH$_4$OH) showed remaining product in the aqueous phase, the water was evaporated and the resulting residue was extracted with CHCl$_3$. The combined organic phases were dried (MgSO$_4$) and evaporated leaving 401 mg of desired phenol title product (91% yield); IR (neat. CM$^{-1}$): 2210.

EXAMPLE 23d

3-[5-Methoxy-2-(phenylethynyl)phenyl]-N,N-dimethylpropanamine

To a 23° C., solution of the enone product of Example 23a (1.46 g, 4.92 mmol) in MeOH (22 mL) was added concentrated HCl (2 mL) with stirring. After stirring at 23° C. for 5 hr, the reaction was quenched by addition of K$_2$CO$_3$ (2.8 g, 20 mmol) and MeOH (10 mL). After stirring for 3 hr, the pH was adjusted to 8 with 3N HCl. The reaction was then filtered and evaporated leaving a brown oil. Column chromatography (flash SiO$_2$; 20% MeOH/CHCl$_3$ and 0.1% NH$_4$OH) gave first 70 mg of the aromatic anisole title product (5% yield) followed by 270 mg of a non-aromatic tri-methoxy compound (15% yield) and finally 1.02 g of a ketone.

EXAMPLE 24

5-[2-(N,N-Dimethylamino)propyl]-4-hydroxy-4-(phenylethynyl)-2-cyclohexen-1-one (steps (a) and (b) at 0° C.)

To a 0° C. solution of p-benzoquinone (1.06 g, 9.79 mmol) in THF (50 mL), was added by cannula solution of lithium phenylacetylide (9.79 mmol; generated as described in Example 23a) in THF (25 mL). After stirring at 0° C. for 15 min, a solution of the Grignard BrMg(CH$_2$)$_3$N(CH$_3$)$_2$ (12.2 mL), 1.6M in THF) and N,N-dimethyl-3,4,5,6-tetrahydro-2(1H)-pyrimidinone (13.5 mL, 112 mmol) was added by cannula. The ice bath was then removed and the reaction was allowed to warm to 23° C. and stir for 1 hr. At this time, TLC (30% EtOAc/hexane) showed no remaining dienone. The reaction was quenched by addition to H$_2$O and Et$_2$O. An emulsion formed which was broken up by addition of saturated NH$_4$Cl. After back extracting the aqueous phase with Et$_2$O (3 times), the combined organic phases were dried (MgSO$_4$) and evaporated leaving a dark brown oil. Column chromatography (flash SiO$_2$, 20% MeOH/CHCl$_3$ and 0.1% NH$_4$OH) of this oil gave 1.12 g of desired title product as a brown gum which crystallized on standing (39% yield).

EXAMPLE 25

4-Hydroxy-5-methyl-4-(phenylethynyl)-2-cyclohexen-1-one (Formula (V), Ar¹=phenyl, R=CH₃)

Phenylacetylene (1 mL, 9.3 mmole, 1 eq) in 10 mL of dry THF (distilled over Na) was introduced into a three-necked 50 mL flask fitted with a mechanical stirrer, thermometer and argon cap. The solution was cooled to $-78°$ C. and treated with 5.8 mL (9.3 mmole, 1 eq) of 1.6M n-butyllithium in hexane. The reaction mixture was stirred at $-78°$ C. for ½ hr, warmed to 0° C. for ½ hr, re-cooled to $-78°$ C. and added via cannula to a solution of 1 g (9.3 mmole, 1 eq) of 1,4-benzoquinone in 20 mL THF, cooled to $-78°$ C. The reaction mixture turned a deep-blue color. The reaction mixture stirred for 20 min at $-78°$ C., 18 mL (0.15 mole, 16 eq) of DMPU was added, the reaction was stirred for 5 min and 3.6 mL (10.2 mole, 1.1 eq) of 2.8M methylmagnesium bromide was added to the reaction which was stirred at $-78°$ C. for 1 hr, allowed to warm to RT and stirred overnight at RT. The reaction mixture was quenched with 100 mL saturated NH₄Cl, extracted three times with 75 mL of EtOAc, the organic layers were combined, washed four times with 75 mL H₂O, once with 75 mL brine, dried (Na₂SO₄), filtered and the solvents evaporated to give 2.2 g of brown oil (HPLC corrected yield of desired product was 67.5%).

What is claimed is:

1. A process for preparing an acetylene of the following Formula (I):

$$X \text{—} \underset{R}{\bigodot} \text{—} C \equiv C \text{—} Ar^1 \quad (I)$$

wherein
X is hydroxy, alkoxy of about 1 to 6 carbons or alkanoyloxy of about 2 to 6 carbons;
Ar¹ is phenyl which may be independently substituted by one or more of alkyl, alkoxy, alkylthio, dialkylamino, halogen or fluoroalkyl; alkyl; cycloalkyl; or alkyl substituted by dialkylamino, cycloalkyl, alkoxy, phenyl or phenyl substituted by 1 to 3 Y groups; and Y is independently alkyl, alkoxy, alkylthio, dialkylamino or halogen or methylenedioxy or ethylenedioxy at adjacent ring carbons; and
R is a substituted or unsubstituted alkyl group of about 1 to 16 carbons,
which comprises the steps of:
(a) reacting an acetylide (II) with a benzoquinone (III):

$$M\text{—}C\equiv C\text{—}Ar^1 \quad O=\bigodot=O$$
(II) \qquad\qquad (III)

wherein M is a moiety containing a metal atom directly attached to the acetylenic carbon, by 1,2-addition at about $-100°$ C. to $+25°$ C. to form a carbinol alkoxide (IV):

$$\underset{O^\ominus M^\oplus}{\bigodot}\overset{C\equiv C\text{—}Ar^1}{} \quad (IV)$$

(b) reacting the alkoxide (IV) with an R-containing organomagnesium reagent to form enone (V) by 1,4-addition at about $-100°$ C. to $+25°$ C.:

$$O=\underset{R}{\bigodot}\overset{C\equiv C\text{—}Ar^1}{\underset{OH}{}} \quad (V)$$

and
(c) dehydrating and aromatizing the enone (V) by heating in the presence of an acid, base or salt to form an X group to yield the acetylene (I).

2. The process of claim 1, wherein steps (a) and (b) are conducted sequentially in the same vessel.

3. The process of claim 1, wherein step (a) is conducted at about $-30°$ C. to 0° C.

4. The process of claim 1, wherein in step (a), M is an alkali metal or contains magnesium directly attached to the acetylenic carbon.

5. The process of claim 1, wherein in step (a), M is lithium, sodium, potassium, magnesium bromide, magnesium chloride or magnesium iodide.

6. The process of claim 1, wherein step (b) is conducted at about $-30°$ C. to $+25°$ C.

7. The process of claim 1, wherein in said step (b), the R-containing organomagnesium reagent is a substituted or unsubstituted alkyl magnesium halide or a di(substituted or unsubstituted alkyl) magnesium compound.

8. The process of claim 1, wherein in said step (b), the R-containing organomagnesium reagent is an R-Mg-halide or an R₂Mg compound.

9. The process of claim 1, wherein in said step (b) the R-containing organomagnesium reagent is an alkyl magnesium chloride or bromide or a dialkyl magnesium compound wherein said alkyl groups are unsubstituted or are substituted with an alkenyl group, a dialkylamino group, a N-alkyl, N-phenylalkyl group, wherein the phenyl is unsubstituted or substituted, or a masked ketone.

10. The process of claim 1, wherein said step (c) is conducted by heating the enone (V) at about 25° to 150° C.

11. The process of claim 1, wherein said step (c) is conducted in the presence of water to provide X as hydroxy, an alkanol to provide X as alkoxy or an alkanoic acid anhydride or halide to provide X as alkanoyloxy.

12. The process of claim 1, further comprising the step of converting (I) wherein R is other than an amino-substituted alkyl group to (I) wherein R is an amino-substituted alkyl group.

13. The process of claim 1, wherein R is a masked 1-(3-butanone).

14. The process of claim 1, wherein X is methoxy, Ar¹ is unsubstituted phenyl and R is a ketal of 1-(3-butanone).

15. The process of claim 1, wherein R is N-[2-(3,4-dimethoxyphenyl)ethyl]-N,α-dimethylpropanamine.

16. The process of claim 1, wherein step (c) is conducted in the presence of pyridinium chloride.

17. The process of claim 1, wherein R is a branched or straight chain alkyl of about 1 to 16 carbons and substituted with one or more of alkenyl; a masked ketone; a masked aldehyde; a dialkylamino group; a (phenylalkyl)alkylamino group; or a (phenylalkyl)alkylamino group wherein the phenyl is substituted by 1, 2, or 3 alkyl or alkoxy groups.

18. The process of claim 1, wherein R is of the formula (VI):

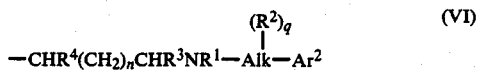

wherein
$R^1$ is alkyl, cycloalkyl or cycloalkylalkyl, or $R^1$ is independently selected from the group consisting of the defined values of —Alk—$Ar^2$;
$R^2$ is independently alkyl or phenyl;
Alk is straight chain alkylene of about 1 to 4 carbons;
q is 0, 1 or 2 or 3 if Alk is alkylene of about 2 to 4 carbons;
$Ar^2$ is a phenyl, phenoxy, thiophenoxy, naphthyl or a 5- or 6-membered heterocyclic aromatic ring which rings may be substituted independently by one or more of alkyl, alkoxy, alkylthio, halogen, fluoroalkyl or dialkylamino or by methylenedioxy at adjacent ring carbons;
$R^3$ is hydrogen, alkyl or alkoxyalkyl;
n is 0, 1 or 2; and
$R^4$ is hydrogen or alkyl.

19. The process of claim 1, wherein the carbinol alkoxide (IV) formed in step (a) is protonated to yield the dienone of formula (VII):

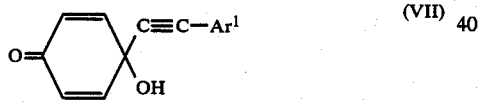

and subsequently deprotonated the dienone to reform the alkoxide (IV).

20. An enone of the following formula (V):

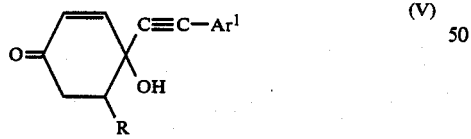

wherein
$Ar^1$ is phenyl which may be independently substituted by one or more of alkyl, alkoxy, alkylthio, dialkylamino, halogen or fluoroalkyl; alkyl; cycloalkyl; or alkyl substituted by dialkylamino, cycloalkyl, alkoxy, phenyl or phenyl substituted by 1 to 3 Y groups; and Y is independently alkyl, alkoxy, alkylthio, dialkylamino or halogen or methylenedioxy or ethylenedioxy at adjacent ring carbons; and
R is substituted or unsubstituted alkyl group of about 1 to 16 carbons.

21. The process of claim 1, wherein said step (b) is conducted in the absence of copper ion.

22. The enone of claim 20, wherein $Ar^1$ is unsubstituted phenyl.

23. The enone of claim 20, wherein R is a substituted or unsubstituted alkyl group of about 1 to 16 carbons wherein the substitution on the alkyl group is one or more of alkenyl, a masked ketone, a masked aldehyde, a dialkylamino group, a (phenylalkyl)alkylamino group or a (phenylalkyl)alkylamino group wherein the phenyl is substituted by 1, 2 or 3 alkyl or alkoxy groups.

24. The enone of claim 23, wherein R is a substituted or unsubstituted alkyl group of about 1 to 16 carbons, wherein said substitution is one or more of alkenyl of about 1 to 4 carbons, a ketal, an acetal, a dialkylamino group of about 1 to 6 carbons in each alkyl, a (phenylalkyl)alkylamino group of about 1 to 4 carbons in the alkyl groups or a (phenylalkyl)alkylamino group of about 1 to 4 carbons in the alkyl groups where the phenyl is substituted by 1, 2 or 3 alkyl or alkoxy groups of about 1 t 6 carbons each.

25. The enone of claim 24, wherein said ketal is a divalent group attached to a non-terminal carbon and has the formula —O—A—O— and said acetal group is of the formula —C(O—A—O)H wherein A is an alkylene of 2 or 3 carbons which is unsubstituted or substituted by one or more alkyls of 1 to 6 carbons each.

26. The enone of claim 20, wherein
$R^1$ is alkyl, cycloalkyl or cycloalkylalkyl, or $R^1$ is independently selected from the group consisting of the defined values of —Alk—$Ar^2$;
$R^2$ is independently alkyl or phenyl;
Alk is straight chain alkylene of about 1 to 4 carbons;
q is 0, 1 or 2 or 3 if Alk is alkylene of about 2 to 4 carbons;
$Ar^2$ is a phenyl, phenoxy, thiophenoxy, naphthyl, or a 5- or 6-membered heterocyclic aromatic ring which rings may be substituted independently by one or more of alkyl, alkoxy, alkylthio, halogen, fluoroalkyl or dialkylamino or by methylenedioxy at adjacent ring carbons;
$R^3$ is hydrogen, alkyl or alkoxyalkyl;
n is 0, 1 or 2; and
$R^4$ is hydrogen or alkyl.

27. The enone of claim 26, wherein
$R^1$ is alkyl of about 1 to 6 carbons, cycloalkyl of about 3 to 6 carbons, cycloalkylalkyl of about 4 to 7 carbons, or $R^1$ is independently selected from the group consisting of the defined values of —Alk—$Ar^2$;
$R^2$ is independently alkyl of about 1 to 4 carbons or phenyl;
Alk is straight chain alkylene of about 1 to 4 carbons;
q is 0, 1 or 2 or 3 if Alk is alkylene of about 2 to 4 carbons;
$Ar^2$ is phenyl, phenoxy, thiophenoxy, naphthyl or a 5- or 6-membered heterocyclic aromatic ring having 1 nitrogen, sulfur or oxygen atom, which rings may be substituted independently by one or more of alkyl of about 1 to 6 carbons, alkoxy or about 1 to 6 carbons, alkylthio of about 1 to 6 carbons, fluoro, chloro, bromo, fluoroalkyl of about 1 to 6 carbons or dialkylamino of about 2 to 12 carbons or methylenedioxy at adjacent ring carbons;
$R^3$ is hydrogen, alkyl of about 1 to 6 carbons or alkoxyalkyl of about 1 to 6 carbons in each alkyl portion;
n is 0, 1 or 2; and
$R^4$ is hydrogen or alkyl of about 1 to 6 carbons.

28. The process of claim 17, wherein R is a branched or straight chain alkyl of about 1 to 16 carbons and substituted with one or more of alkenyl of about 1 to 4 carbons; a ketal; an acetal; a dialkylamino group of about 1 to 6 carbons in each alkyl; a (phenylalkyl)alkylamino group of about 1 to 4 carbons in the alkyl groups; or a (phenylalkyl)alkylamino group of about 1 to 4 carbons in the alkyl groups wherein the phenyl is substituted by 1, 2 or 3 alkyl or alkoxy groups of about 1 to 6 carbons each.

29. The process of claim 17, wherein R is a branched or straight chain alkyl of about 1 to 16 carbons substituted by one substituent.

30. The process of claim 1, wherein $Ar^1$ is unsubstituted phenyl.

31. The process of claim 28, wherein said ketal is a divalent group attached to a non-terminal carbon and has the formula —O—A—O— and said acetal group is of the formula —C(O—A—O)H wherein A is an alkylene of 2 or 3 carbons which is unsubstituted or substituted by one or more alkyls of 1 to 6 carbons each.

32. The process of claim 18, wherein $R^1$ is alkyl of abouts 1 to 6 carbons, cycloalkyl of about 3 to 6 carbons, cycloalkylalkyl of about 4 to 7 carbons, s or $R^1$ is independently selected from the group consisting of the defined values of —Alk—$Ar^2$;

$R^2$ is independently alkyl of about 1 to 4 carbons or phneyl;

Alk is straight chain alkylene of about 1 to b 4 carbons;

q is 0, 1 or 2 or 3 if Alk is alkylene of about 2 to 4 carbons;

$Ar^2$ is phenyl, phenoxy, thiophenoxy, naphthyl or a 5- or 6-membered heterocyclic aromatic ring having 1 anitrogen, sulfur or oxygen atom, which rings may be substituted independently by one or more of alkyl of about 1 to 6 carbons, alkoxy of about 1 to 6 carbons, alkylthio of about 1 to a6 carbons, fluoro, chloro, bromo, fluoroalkyl of about 1 to 6 carbons or dialkylamino of about 2 to 12 carbons or methylenedioxy at adjacent ring carbons;

$R^3$ is hydrogen, alkyl of about 1 to 6 carbons or alkoxyalkyl of about 1 to 6 carbons in each alkyl portion;

n is 0, 1 or 2; and $R^4$ is hydrogen or alkyl of about 1 to 6 carbons.

* * * * *